United States Patent [19]

Franetzki

[11] Patent Number: 5,661,519
[45] Date of Patent: Aug. 26, 1997

[54] VIDEO CAMERA FASHIONED AS A HANDPIECE FOR OBSERVING SUBJECTS IN MOUTH OF A PATIENT

[75] Inventor: Manfred Franetzki, Bensheim, Germany

[73] Assignee: Siemens Aktiengesellschaft, Munich, Germany

[21] Appl. No.: 381,979

[22] PCT Filed: Aug. 13, 1993

[86] PCT No.: PCT/DE93/00732

§ 371 Date: Feb. 13, 1995

§ 102(e) Date: Feb. 13, 1995

[87] PCT Pub. No.: WO94/04068

PCT Pub. Date: Mar. 3, 1994

[30] Foreign Application Priority Data

Aug. 14, 1992 [DE] Germany .......................... 42 26 990.3

[51] Int. Cl.$^6$ ............................................. H04N 7/18
[52] U.S. Cl. .................. 348/66; 348/65; 348/77; 433/29
[58] Field of Search .................. 348/65, 66, 77, 348/67; 433/29, 41, 42, 43, 121, 122, 123

[56] References Cited

U.S. PATENT DOCUMENTS

| | | | |
|---|---|---|---|
| 3,976,982 | 8/1976 | Eiselen . | |
| 4,727,416 | 2/1988 | Cooper et al. | 348/65 |
| 4,730,909 | 3/1988 | Takahashi | 348/66 |
| 4,746,203 | 5/1988 | Nishioka et al. . | |
| 4,858,001 | 8/1989 | Milbank et al. | 348/65 |
| 4,890,159 | 12/1989 | Ogiu . | |
| 4,891,696 | 1/1990 | Miyazaki . | |
| 4,894,715 | 1/1990 | Uchikubo et al. | 348/66 |
| 4,899,731 | 2/1990 | Takayama et al. | 348/65 |
| 4,989,083 | 1/1991 | Eino | 348/65 |
| 5,005,943 | 4/1991 | Fort | 128/4 |
| 5,027,138 | 6/1991 | Gandrud | 354/62 |
| 5,049,070 | 9/1991 | Ademovic | 433/29 |
| 5,124,789 | 6/1992 | Hiyama et al. | 348/65 |
| 5,124,797 | 6/1992 | Williams et al. | 358/225 |
| 5,156,141 | 10/1992 | Krebs et al. | 128/4 |
| 5,178,536 | 1/1993 | Werly et al. | 433/29 |
| 5,243,967 | 9/1993 | Hibino | 348/65 |
| 5,251,356 | 10/1993 | Oaki et al. | 348/65 |
| 5,313,306 | 5/1994 | Kuban et al. | 348/65 |
| 5,487,661 | 1/1996 | Peithman | 433/29 |

FOREIGN PATENT DOCUMENTS

| | | |
|---|---|---|
| 0 389 453 | 9/1990 | European Pat. Off. . |
| 41 02 196 | 8/1991 | Germany . |

OTHER PUBLICATIONS

Abstract of Japanese Published Application 60–217326, *Patent Abstracts of Japan*, vol. 10, No. 80 (P–441) [2137] Mar. 29, 1986.

Martinez, "Image Rotation", *IBM Technical Disclosure Bulletin*, vol. 27, No. 1B, Jun. 1984, pp. 510–511.

Primary Examiner—Howard W. Britton
Assistant Examiner—Wand Rao
Attorney, Agent, or Firm—Hill, Steadman & Simpson

[57] ABSTRACT

A number of solutions are presented for an image rectification, i.e. a realistic alignment of the image given employment of an intraoral camera. To this end, arrangement is present that reproduce the image on a monitor erect and non-reversed regardless of the sightline of the camera.

10 Claims, 2 Drawing Sheets

Observation of the Lower Jaw:

| plan view | right | no image influencing |
|---|---|---|
| | left | no image influencing |
| side view | outside right | 90° counter-clockwise rotation |
| | outside left | 90° clockwise rotation |
| | inside right | 90° clockwise rotation |
| | inside left | 90° counter-clockwise rotation |
| frontal view | | no image influencing |

Observation of the Upper Jaw:

| plan view | right | image mirroring |
|---|---|---|
| | left | image mirroring |
| side view | outside right | 90° counter-clockwise rotation |
| | outside left | 90° clockwise rotation |
| | inside right | 90° clockwise rotation |
| | inside left | 90° counter-clockwise rotation |
| frontal view | | no image influencing |

Observation of the Lower Jaw:

| plan view | right | no image influencing |
|---|---|---|
| | left | no image influencing |
| side view | outside right | 90° counter-clockwise rotation |
| | outside left | 90° clockwise rotation |
| | inside right | 90° clockwise rotation |
| | inside left | 90° counter-clockwise rotation |
| frontal view | | no image influencing |

Observation of the Upper Jaw:

| plan view | right | image mirroring |
|---|---|---|
| | left | image mirroring |
| side view | outside right | 90° counter-clockwise rotation |
| | outside left | 90° clockwise rotation |
| | inside right | 90° clockwise rotation |
| | inside left | 90° counter-clockwise rotation |
| frontal view | | no image influencing |

FIG 1

VIDEO CAMERA FASHIONED AS A HANDPIECE FOR OBSERVING SUBJECTS IN MOUTH OF A PATIENT

BACKGROUND OF THE INVENTION

The invention is directed to a video camera fashioned as a handpiece for observing subjects in the mouth of a patient.

Given employment of a video camera as disclosed, for example, by U.S. Pat. No. 4,727,416 or U.S. Pat. No. 5,049,070, the information about the subject position and viewing direction is naturally lacking a priori at the picture screen. The subject always appears at the same location with the same alignment on the picture screen.

EP-0 389 453 discloses an endoscope proposed for dental employment, whereby the image is picked up via a fiberoptics and is supplied to a telecamera. The telecamera is arranged externally from the hand instrument and forwards the image information acquired thereat to a monitor. The end piece of the hand instrument introducible into the patient's mouth can be turned or bent relative to the fiberoptics around the longitudinal axis thereof. It is thus possible to reproduce the images erect on the monitor without the connecting cable together with the fiberoptics having to be turned for this purpose between handpiece and camera. The subject appears on the monitor at the same location having the same alignment on the picture screen, i.e. a tooth in the left half of the lower jaw likewise appears on the left side on the monitor but mirror-inverted. The same is true of the upper jaw. The dentist thus sees the image on the monitor in the same way that he would see it with a small mirror with which he observes the subject in the patient's mouth.

The same is also true of the endoscoping system disclosed by U.S. Pat. No. 4,890,159 which comprises a plurality of differently fashioned endoscopes that can be alternatively connected to a central image processing unit. The electronics of the image processing unit is constructed such that an erect or mirror-inverted video image can be reproduced at the monitor regardless of whether an endoscope having frontal or lateral image acquisition optics or an endoscope having long or short image transducer is connected to the input of the image processing unit.

U.S. Pat. No. 4,858,001 discloses that the endpiece of the hand instrument be fashioned rotatable relative to the remaining optics in order to thus be able to display the subject on the picture screen turned relative to the observer. Although such an arrangement makes it possible to correctly reproduce the side position, it does not make it possible to reproduce the position distal/proximal in a realistic fashion given a change from lower jaw to upper jaw or vestibular to lingual.

The same is true given employment of a calculating program known from the technical literature R. T. Martinez, "Image Rotation", *IBM Technical Disclosure Bulletin* vol. 27, no. 1B, June 1984, pp. 510/511), wherein it is proposed that the image raster be electronically turned in an electronic way with the assistance of a computer program.

U.S. Pat. No. 3,976,982 discloses an apparatus that makes it possible to manipulate images in an electronic way, in that the images that are represented in the form of two-dimensional arrays are supplied to an electronics wherein the images can be turned or mirrored in an electronic way.

Such observations may be acceptable for simple inspections. When, however, an instrument is to be guided given indirect treatment upon observation of the picture screen, it is difficult for the user to implement work in the patient's mouth with the camera and looking exclusively at the monitor. Alternate work when looking at the monitor and at the camera would mean constant readjustment.

SUMMARY OF THE INVENTION

An object of the present invention is to provide an improved video camera for insertion into a mouth of a patient and connected to a monitor to display an image of the subject or object in the mouth of the patient.

According to the invention, an apparatus includes a monitor connected to a video camera which is constructed as a handpiece with either an objective and image transducer being rotatable in common or the objective being rotatable on a non-rotatable part of the handpiece that contains the image transducer (for example, CCD) of the camera, which has means for acquiring the rotational position of the objective. A device is also present which reproduces the image on a monitor erect and non-reversed regardless of the sightline of the camera, and an additional means for acquiring the sightline of the camera is either integrated in the camera or a further means is present with which the sightline of the camera can be manually input. Finally, means is provided with which the image on the monitor can be rotated or mirrored. The subject can thus be realistically displayed, i.e. practically in the same way that the physician sees the subject in the mouth with his naked eye.

The apparatus can alternatively contain means for mirroring the monitor image for the purpose of an erect and non-reversed playback, said means being capable of being activated by the user, for example with the assistance of a switch, so that treatment from the front with the monitor behind the patient as well as indirect treatment from behind with the monitor in front of the patient are enabled.

This specifically means that, for example given a movement of the camera toward the left, the image on the picture screen moves toward the left, as though, for instance, an occlusion is observed in the upper jaw or lower jaw. Given a downward movement, the picture on the screen moves downward, whether the tooth is viewed vestibularly or lingually. Given a distal movement, an occlusion surface on the screen always moves in the same direction, for example upward, regardless of whether the upper jaw or lower jaw is observed.

BRIEF DESCRIPTION OF THE DRAWINGS

FIG. 1 is a table showing the types of image influencing with different observations of the jaw;

DESCRIPTION OF THE PREFERRED EMBODIMENTS

Figure 2:
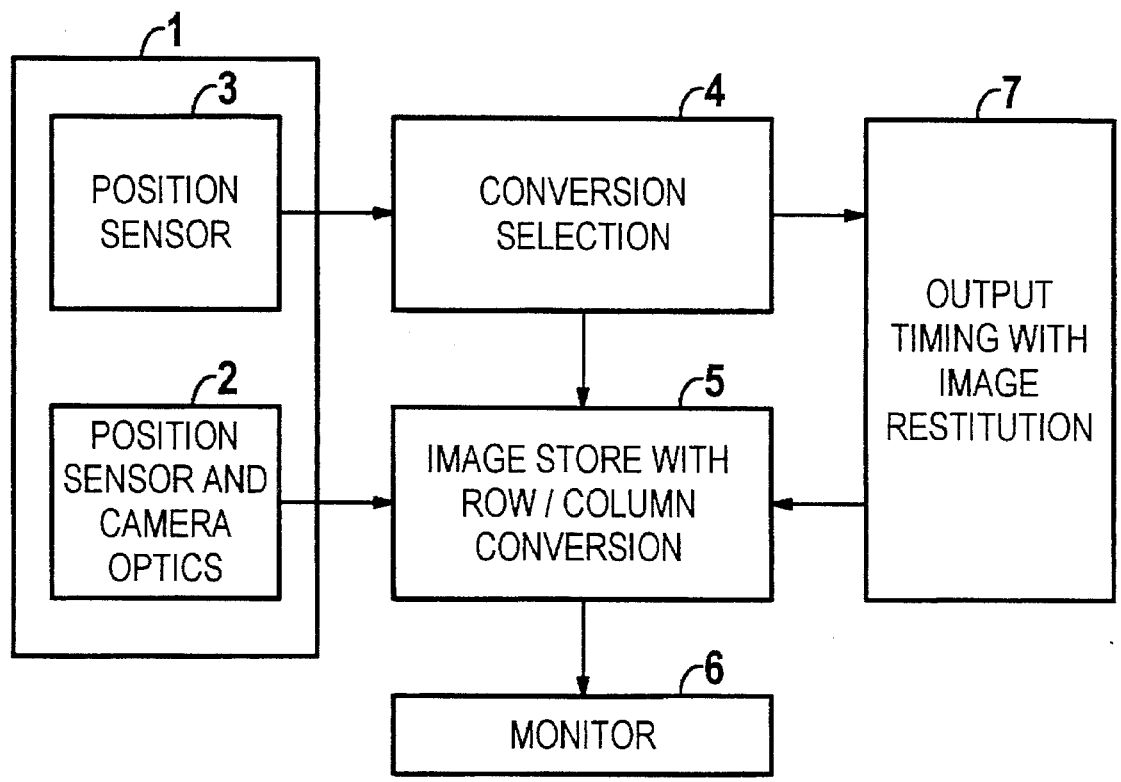
FIG. 2 is a block diagram of the apparatus according to the present invention.

The invention discloses three solutions, whereby a camera having an elongated, endoscope-like objective put in place thereon is employed in all three embodiments.

Solution 1

A CCD is provided as an image transducer, this being non-rotatably connected to a cable that can likewise not be rotated. The objective can be locked in four positions rotated by 90°. The locked position is recognized by a sensor, for example a switch contact, and is conducted to a control electronics. The image is processed unmodified in two of the four locked positions and is processed mirrored in the other 2 locked positions (for example, by reversing the read-out direction of the image store).

Solution two

In this solution, the image mirroring is not electronically achieved as in the case of solution 1 but on the basis of selectively hinging a reversing prism or a mirror into or out of the beam path of the objective in a known way.

Analogously, these solutions can also be realized in conjunction with a fiber bundle whose bending direction is acquired with a sensor.

Solution 3

In this embodiment, the image transducer turns together with the objective, i.e. image transducer (for example, CCD) and objective are rigidly coupled to one another. The visual angle of the camera relative to the perpendicular is acquired and the image is correspondingly rotated on the picture screen of the monitor with electronic means. The acquisition of the rotational angle ensues on the basis of an angle transmitter, whereby the perpendicular direction is prescribed by the force of gravity of a weight eccentrically secured to the axis thereof in rotatable fashion. The angle transmitter can, for example, be a rotary potentiometer or a digital transmitter (incremental transmitter). The axis of the angle transmitter lies parallel to the longitudinal axis of the objective. The rotation of the image ensues corresponding to the signal of the angle transmitter by re-processing the primary image read from the CCD into the image store with hardware and/or software means.

The angle measurement and corresponding image rotation can occur continuously or, preferably, can only be a detection of the four quadrants with corresponding, electronic mirroring of the image (transposition of the read-out direction of rows or columns in the CCD or in the image store).

The automatic detection of the four positions, sightline upward, downward, toward the left and right, can be replaced in a simpler case with a manual input at the apparatus, for example with a 4-position switch.

According to a further development, an advance image mirroring is provided. The advance image mirroring is not activated when the attending person is seated in front of the patient and the picture screen is located behind the patient (work in direct view) and is activated when the attending physician is seated behind the patient and the picture screen is located over the patient (work in a mirror).

This mirroring can again occur optically in the objective or electronically (read-out reversal of the columns).

The real-time image processing of a positionally adapted intraoral camera given an erectly seated patient and an observation on a segment extending between 8:00 and 9:00 of, on the one hand, the upper jaw and, on the other hand, the lower jaw is shown with reference to FIG. 1. It proceeds from the overview that no image influencing is necessary given a plan view onto the tooth, i.e. a tooth or, respectively, a row of teeth in the right-hand mandibular arch is imaged at the picture screen in the same way that the camera or, respectively, an observer sees it in plan view. The same is true for the observation of the left half of the lower mandibular arch.

Given a side view, an image rotation by 90° in a clockwise sense or in a counter-clockwise sense ensues dependent on the observation (right/left—outer/inner). As can be easily imagined, an image influencing is again not carried out given a frontal view.

The analogous case applies to the observation of the upper jaw.

The function and the interaction of the provided means shall be set forth in greater detail with reference to the block circuit diagram of FIG. 2.

The camera shown as a block or box 1 contains an image sensor shown as a box 2 in the box, having an electronics, an optics with illumination and a positional or position sensor shown as box 3 that recognizes four discrete camera attitudes, preferably in steps of 90°.

A conversion selection 4 generates signals suitable for an image store 5 from the signals of the positional sensor 3. As a result thereof, the image store is configured such that the respectively required adaptation (rotation, mirroring according to the table in FIG. 1) occurs.

The image store 5 has two jobs: it serves, on the one hand, as intermediate storage and, on the other hand, serves the purpose of generating a still image at the monitor 6. An intermediate storage is required for rotation or mirroring of a "real time image". The manipulated image is thereby displayed temporally offset by 1 frame.

A still image arises as a result of a permanent read-out, whereby 1 stored image remains in the store without a new image being read in.

A block 7 is an output timing with image restitution or rectification and is only required given rotation by ±90°. Since the monitor image or, respectively, sensor image usually comprises a side ratio of 4:3, an adaptation to the monitor is required given rotation by ±90°. Two different matching forms fundamentally derive therefrom, namely a matching to the two lateral image edges and to the upper and lower image edge. Whereas a complete image yields black stripes at the edges in the one instance, image information at the upper and lower edge are lost given an enlarged image, whereby, however, the monitor area is fully utilized. Since a scale modification (enlargement, diminution) ensues in both instances, the output timing must be correspondingly modified via the block 7.

Figure 3:
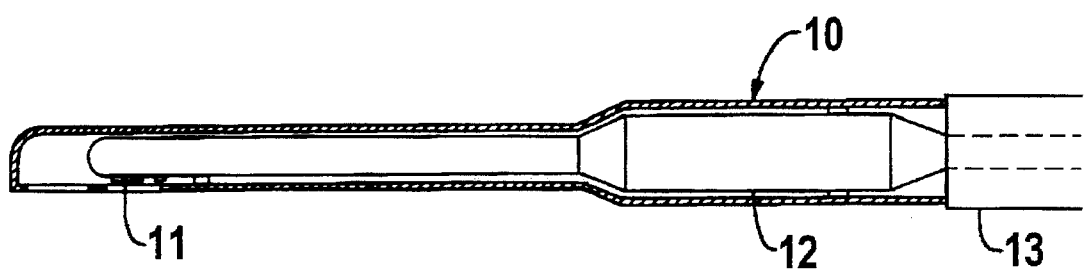
FIG. 3 is a side view of a handpiece having a video camera of the present invention.

The video camera 1 can be fashioned as a handpiece 10 (FIG. 3) for observing subjects or objects in a mouth of a patient and displaying an image of the subject on a monitor 6 (FIG. 2). An objective 11 of the camera is mounted in a part 12 of the handpiece 10, and the part 12 is mounted for rotation on a non-rotatable part 13. The image transducer may be in the part 12 to be rotated in common with the objective 11 or may be in the non-rotatable part 13.

I claim:

1. Video camera fashioned as a handpiece for observing subjects in a mouth of a patient and displaying an image of the subject on a monitor, said camera including an objective connected to an image transducer (for example CCD) of the camera, said objective and image transducer being mounted for rotation together in the handpiece, first means for acquiring a rotational position of the objective and image transducer, said first means including an angle transmitter for continually acquiring an angle relative to the perpendicular, said angle transmitter being composed of a weight eccentrically secured to an axis of a potentiometer or digital angle sensor, second means for reproducing the image on a monitor erect and non-reversed regardless of a sightline of the camera, additional means for providing the sightline of the camera and third means for turning or mirroring the image on the monitor.

2. Video camera according to claim 1, wherein electronic means are provided.

3. Video camera according to claim 1, wherein said third means are opto-mechanical means, for example hinged reversing prisms or mirrors, provided in a beam path of the camera.

4. Video camera according to claim 1, wherein the setting an acquisition ensues in four basic directions of downward, upward, left or right.

5. Video camera according to claim 1, wherein the rotational position in 4 locked positions is acquired with an electronic means, for example a microswitch or a light barrier.

6. Video camera according to claim 1, wherein the additional means is built into the camera.

7. Video camera according to claim 1, wherein the addtional means enables manual input of the sightline into the camera.

8. Video camera fashioned as a handpiece for observing subjects in a mouth of a patient and displaying the subject or an image in a monitor, said camera including first means to reproduce the image erect and non-reversed on a monitor regardless of a sightline of the camera, second means for mirroring the monitor image for the purpose of the respectively non-reversed presentation, said second means being capable of being activated by a user, for example with the assistance of a switch, so that both treatment from the front with the monitor behind the patient as well as indirect treatment from behind with the monitor in front of the patient are enabled.

9. Video camera according to claim 8, wherein said camera includes an objective connected to an image transducer of the camera, said objective and image transducers being mounted for rotation together in the handpiece, and means for acquiring a rotation position of the objective and image transducer including an angle transmitter.

10. Video camera according to claim 9, wherein the angle transmitter is composed of a weight eccentrically secured to an axis of a sensor.

* * * * *